(12) United States Patent
Yasui et al.

(10) Patent No.: US 6,978,203 B2
(45) Date of Patent: Dec. 20, 2005

(54) CONTROLLER FOR CONTROLLING ELEMENT TEMPERATURE OF EXHAUST GAS SENSOR

(75) Inventors: Yuji Yasui, Wako (JP); Hiroshi Kitagawa, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/437,459

(22) Filed: May 14, 2003

(65) Prior Publication Data

US 2004/0016228 A1 Jan. 29, 2004

(30) Foreign Application Priority Data

May 16, 2002 (JP) ........................................ 2002-141659

(51) Int. Cl.$^7$ ............................................. G06F 19/00
(52) U.S. Cl. ......................................... 701/101; 701/103
(58) Field of Search ................................. 701/101, 102, 701/103, 109

(56) References Cited

U.S. PATENT DOCUMENTS

| | | | | |
|---|---|---|---|---|
| 4,765,298 A | * | 8/1988 | Kojima et al. .............. | 123/697 |
| 5,656,190 A | * | 8/1997 | Aoki ........................... | 219/505 |
| 5,731,570 A | * | 3/1998 | Aoki ........................... | 219/497 |
| 5,752,493 A | * | 5/1998 | Abe et al. ................... | 123/686 |
| 6,384,386 B2 | * | 5/2002 | Hashimoto et al. ......... | 219/497 |
| 6,651,639 B2 | * | 11/2003 | Hada et al. ................. | 123/697 |

FOREIGN PATENT DOCUMENTS

JP        2000-304721      11/2000

* cited by examiner

*Primary Examiner*—John T. Kwon
(74) *Attorney, Agent, or Firm*—Squire, Sanders and Dempsey, L.L.P.

(57) ABSTRACT

A controller for controlling a temperature of an element disposed in an exhaust gas sensor is provided. The exhaust gas sensor further comprises a heater for heating the element. The controller comprises a control unit. The control unit performs response assignment control to determine a duty ratio of energization of the heater. In one embodiment, the response assignment control uses a switching function that specifies a response of the element temperature to a target temperature. The energization duty ratio is determined based on the integral of the switching function. In one embodiment, the element temperature of the exhaust gas sensor is estimated. The control unit determines the energization duty ratio of the heater based on the estimated element temperature. The element temperature may be estimated based on the temperature of exhaust gas.

27 Claims, 16 Drawing Sheets

(a)

(b)

CONTROLLER FOR CONTROLLING ELEMENT TEMPERATURE OF EXHAUST GAS SENSOR

BACKGROUND OF THE INVENTION

1. Technical Field

The present invention relates to an apparatus and a method for controlling the temperature of an element of an exhaust gas sensor provided in an exhaust system of an internal combustion engine.

2. Description of the Related Art

A catalyst converter is provided in an exhaust system of an internal combustion engine of a vehicle. When the air-fuel ratio of air-fuel mixture introduced into the engine is lean, the catalyst converter oxidizes HC and CO with excessive oxygen included in the exhaust gas. When the air-fuel ratio is rich, the catalyst converter reduces Nox with HC and CO. When air-fuel ratio is in the stoichiometric air-fuel ratio region, HC, CO and Nox are simultaneously and effectively purified.

An exhaust gas sensor is provided downstream of the catalyst converter. The exhaust gas sensor detects the concentration of oxygen included in the gas discharged into the exhaust system. The detection value of the exhaust gas sensor is used for various control of the internal combustion engine. If response of the exhaust gas sensor deteriorates, the internal combustion engine may not be appropriately controlled, which may cause deterioration in the operating state of the engine.

The output of the exhaust gas sensor varies according to the temperature of an element provided in the exhaust gas sensor. The element is typically zirconium ($ZrO_2$) or titania ($TiO_2$). The air-fuel ratio is controlled by converging the output of the exhaust gas sensor to a desired value. If the element temperature changes, the desired value established for the air-fuel ratio control also changes. In order to implement stable air-fuel control, the element temperature needs to be controlled.

The element is heated by a heater, which is typically provided in the exhaust gas sensor. The element temperature is adjusted by controlling a duty ratio of energization of the heater. For example, the energization duty ratio is determined based on an elapsed time after the engine start.

Japanese Patent Application Unexamined Publication No. 2000-304721 describes another scheme in which an energization duty ratio of the heater is determined by referring to a table or map that is pre-established in accordance with the temperature of an air-fuel ratio sensor. According to the scheme, the energization duty ratio is further corrected in accordance with the operating state (e.g., fuel cut state, idling state) of the engine.

When the element temperature is controlled to a temperature that is different from a temperature used for the normal operating state of the engine, the accuracy of the control for the element temperature needs to be maintained at high level. If the element temperature is not controlled to an appropriate temperature, overshoot or undershoot of the element temperature may occur, which may damage the heater and inactivate the element.

In the above conventional scheme in which the energization duty ratio of the element is determined by referring to the preset table or map, it is difficult to precisely control the element temperature to a desired temperature.

Therefore, there is a need for an apparatus and a method that stably and precisely controls the element temperature of an exhaust gas sensor.

SUMMARY OF THE INVENTION

According to one aspect of the present invention, an apparatus for controlling a temperature of an element disposed in an exhaust gas sensor is provided. The apparatus comprises a control unit configured to perform response assignment control to determine a duty ratio of energization of a heater disposed in the exhaust gas sensor. The response assignment control is performed so that the element temperature converges to a target temperature.

The response assignment control can prevent the element temperature from overshooting and undershooting. The response assignment control can also prevent the exhaust gas sensor from being damaged by excessively high temperature of the element and can prevent the exhaust gas sensor from being inactivated by excessively low temperature of the element. Since the accuracy of the element temperature control is maintained at high level, the durability of the heater is improved.

According to another aspect of the present invention, a switching function for the response assignment control is determined. The switching function specifies a response of the element temperature to a target temperature. The energization duty ratio is determined based on the integral of the switching function.

Variations may occur in the amount of heat from the heater and/or from the element of the exhaust gas sensor. The amount of released heat may vary according to changes in the air temperature. When such variations occur, the use of the integral of the switching function enables the element temperature to be controlled to a target temperature without causing a steady-state error. The response assignment control can suppress variations in the convergence behavior of the element temperature toward the target temperature.

According to another aspect of the present invention, an estimator for estimating the element temperature of the exhaust gas sensor is further provided. The energization duty ratio of the heater is determined based on the estimated element temperature. The energization duty ratio may be determined so that the estimated element temperature converges to a target temperature. Thus, the cost of providing an additional means for directly measuring the element temperature of the exhaust gas sensor is avoided. The estimation of the element temperature enables the element temperature to be controlled with better accuracy. In one embodiment, the element temperature is estimated based on an operating state of the engine.

According to another aspect of the present invention, the element temperature is estimated based on a temperature of exhaust gas. The temperature of exhaust gas may be estimated based on an operating state of the engine. Thus, the cost of providing an additional means for directly measuring the temperature of the exhaust gas is avoided.

The control for the element temperature may be utilized to detect a failure of the exhaust gas sensor. In one embodiment, a failure of the exhaust gas sensor is detected by comparing detection values of the exhaust gas sensor under different element temperatures. In order to generate the states of the different element temperatures, the response assignment control is performed. According to the embodiment, the air-fuel ratio does not need to be manipulated for the purpose of detecting a failure of the exhaust gas sensor. The failure detection can be done without increasing the amount of deleterious substances in the exhaust gas, which would otherwise be produced from manipulation of the air-fuel ratio for the purpose of the failure detection.

DETAILED DESCRIPTION OF THE PREFERRED EMBODIMENTS

Structure of Internal Combustion Engine and Controller

Figure 1:
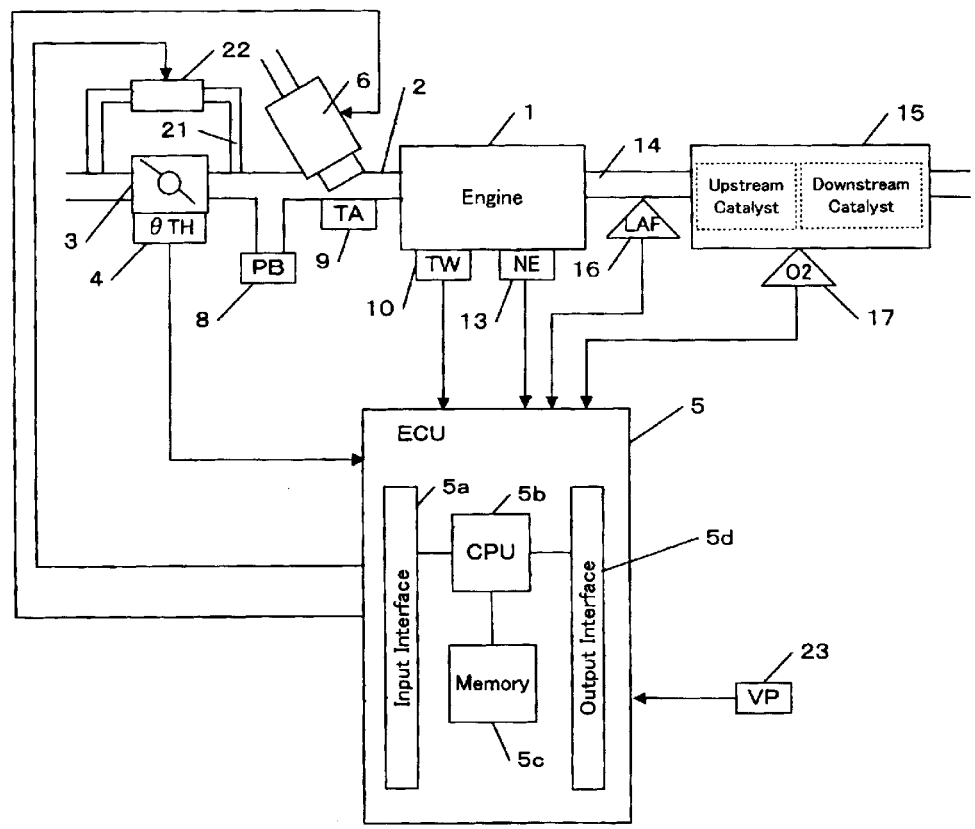
FIG. 1 is a schematic view of an internal combustion engine and its controller according to one embodiment of the present invention.

Preferred embodiments of the present invention will be described referring to the attached drawings. FIG. 1 is a block diagram showing a controller of an internal-combustion engine (hereinafter referred to as an engine) in accordance with one embodiment of the invention.

An electronic control unit (hereinafter referred to as an ECU) 5 comprises an input interface 5a for receiving data sent from each part of the engine 1, a CPU 5b for carrying out operations for controlling each part of the engine 1, a storage device 5c including a read only memory (ROM) and a random access memory (RAM), and an output interface 5d for sending control signals to each part of the engine 1. Programs and various data for controlling each part of the vehicle are stored in the ROM. A program for performing a failure detection process according to the invention, data and tables used for operations of the program are stored in the ROM. The ROM may be a rewritable ROM such as an EEPROM. The RAM provides work areas for operations by the CPU 5a, in which data sent from each part of the engine 1 as well as control signals to be sent out to each part of the engine 1 are temporarily stored.

The engine is, for example, an engine equipped with four cylinders. An intake manifold 2 is connected to the engine 1. A throttle valve 3 is disposed upstream of the intake manifold 2. A throttle valve opening (θ TH) sensor 4, which is connected to the throttle valve 3, outputs an electric signal corresponding to an opening angle of the throttle valve 3 and sends it to the ECU 5.

A bypass passage 21 for bypassing the throttle valve 3 is provided in the intake manifold 2. A bypass valve 22 for controlling the amount of air to be supplied into the engine 1 is provided in the bypass passage 21. The bypass valve 22 is driven in accordance with a control signal from the ECU 5.

A fuel injection valve 6 is provided for each cylinder at an intermediate point in the intake manifold 2 between the engine 1 and the throttle valve 3. The fuel injection valve 6 is connected to a fuel pump (not shown) to receive fuel supplied from a fuel tank (not shown). The fuel injection valve 6 is driven in accordance with a control signal from the ECU 5.

An intake manifold pressure (Pb) sensor 8 and an outside air temperature (Ta) sensor 9 are mounted in the intake manifold 2 downstream of the throttle valve 3. The detected intake manifold pressure Pb and outside air temperature Ta are sent to the ECU 5.

An engine water temperature (TW) sensor 10 is attached to the cylinder peripheral wall, which is filled with cooling water, of the cylinder block of the engine 1. The temperature of the engine cooling water detected by the TW sensor is sent to the ECU 5.

A rotational speed (Ne) sensor 13 is attached to the periphery of the camshaft or the periphery of the crankshaft (not shown) of the engine 1, and outputs a CRK signal pulse at a predetermined crank angle cycle (for example, a cycle of 30 degrees) that is shorter than a TDC signal pulse cycle issued at a crank angle cycle associated with a TDC position of the piston. The CRK pulses are counted by the ECU 5 to determine the rotational speed Ne of the engine 1.

An exhaust manifold 14 is connected to the engine 1. The engine 1 discharges exhaust gas through the exhaust manifold 14. A catalyst converter 15 removes deleterious substances such as HC, CO, and Nox included in exhaust gas flowing through the exhaust manifold 14. The catalyst converter 15 comprises two catalysts, an upstream catalyst and a downstream catalyst.

A full range air-fuel ratio (LAF) sensor 16 is provided upstream of the catalyst converter 15. The LAF sensor 16 linearly detects the concentration of oxygen included in exhaust gas over a wide air-fuel ratio zone, from the rich zone where the air/fuel ratio is richer than the stoichiometric air/fuel ratio to an extremely lean zone. The detected oxygen concentration is sent to the ECU 5.

An O2 (exhaust gas) sensor 17 is provided between the upstream catalyst and the downstream catalyst. The O2 sensor 17 is a binary-type of exhaust gas concentration sensor. The O2 sensor outputs a high level signal when the air-fuel ratio is richer than the stoichiometric air-fuel ratio, and outputs a low level signal when the air-fuel ratio is leaner than the stoichiometric air-fuel ratio. The electric signal is sent to the ECU 5.

The O2 sensor comprises an element and a heater for heating the element. The element is implemented with, for example, zirconium (ZrO2) or titania (TiO2). The heater is connected to an electric circuit. The element temperature can be controlled by energization energy supplied to the heater.

A vehicle speed (VP) sensor 23 for detecting vehicle speed is connected to the ECU 5. The detected vehicle speed signal is sent to the ECU 5.

Signals sent to the ECU 5 are passed to the input circuit 5a. The input interface 5a converts analog signal values into digital signal values. The CPU 5b processes the resulting digital signals, performs operations in accordance with the programs stored in the ROM, and creates control signals. The output interface 5d sends these control signals to actuators for a bypass valve 22, fuel injection valve 6 and other mechanical components.

Figure 2:
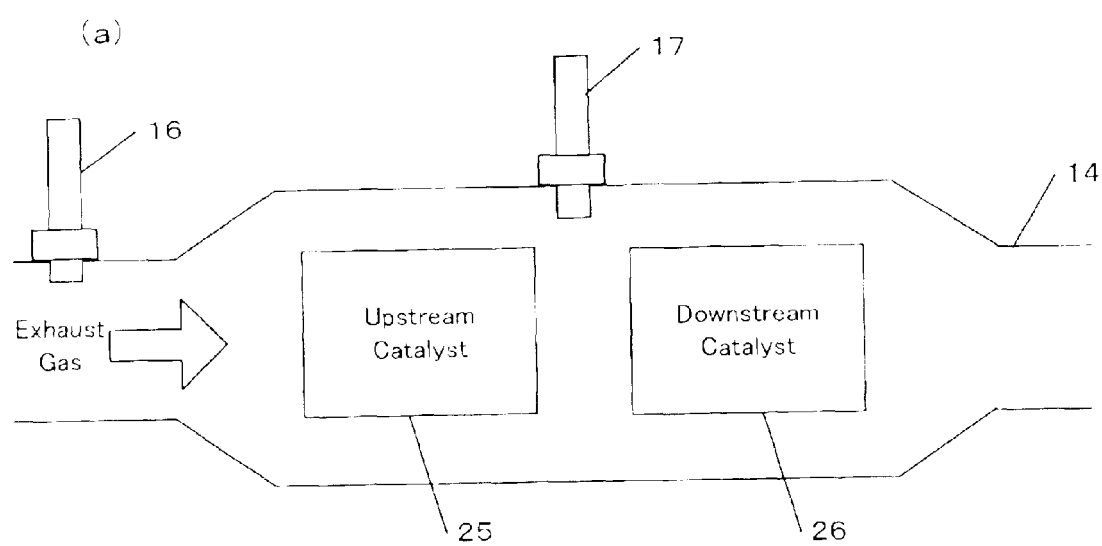
FIG. 2 is a view of layout of a catalyst apparatus and an exhaust gas sensor according to one embodiment of the present invention.
Figure 2:
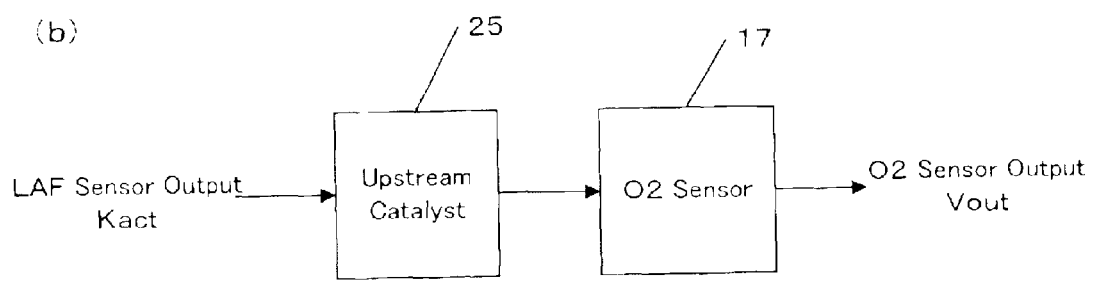

FIG. 2(*a*) shows a structure of the catalyst converter 15. Exhaust gas introduced into the exhaust manifold 14 passes through the upstream catalyst 25 and then through the downstream catalyst 26. It is known that it is easier to maintain the purification rate of Nox at an optimal level by air-fuel ratio control based on the output of an O2 sensor provided between the upstream and downstream catalysts, compared with air-fuel ratio control based on the output of an O2 sensor provided downstream of the downstream catalyst. Therefore, in the embodiment of the invention, the O2 sensor 17 is provided between the upstream and downstream catalysts. The O2 sensor 17 detects the concentration of oxygen included in exhaust gas after the passage through the upstream catalyst 25.

FIG. 2(*b*) is a block diagram showing a system from a LAF sensor 16 to the O2 sensor 17 shown in FIG. 2(*a*). The LAF sensor 16 detects an air-fuel ratio Kact of the exhaust gas supplied to the upstream catalyst 25. The O2 sensor 17 outputs a voltage Vout representing the oxygen concentration of the exhaust gas after the purification by the upstream catalyst 25.

The upstream catalyst 25 and the O2 sensor 17 are disposed in series. There exist delay and dead time of the upstream catalyst 25 and the O2 sensor 17 between an input of the system or the air-fuel ratio Kact and an output of the system or the output Vout of the O2 sensor 17.

Figure 3:
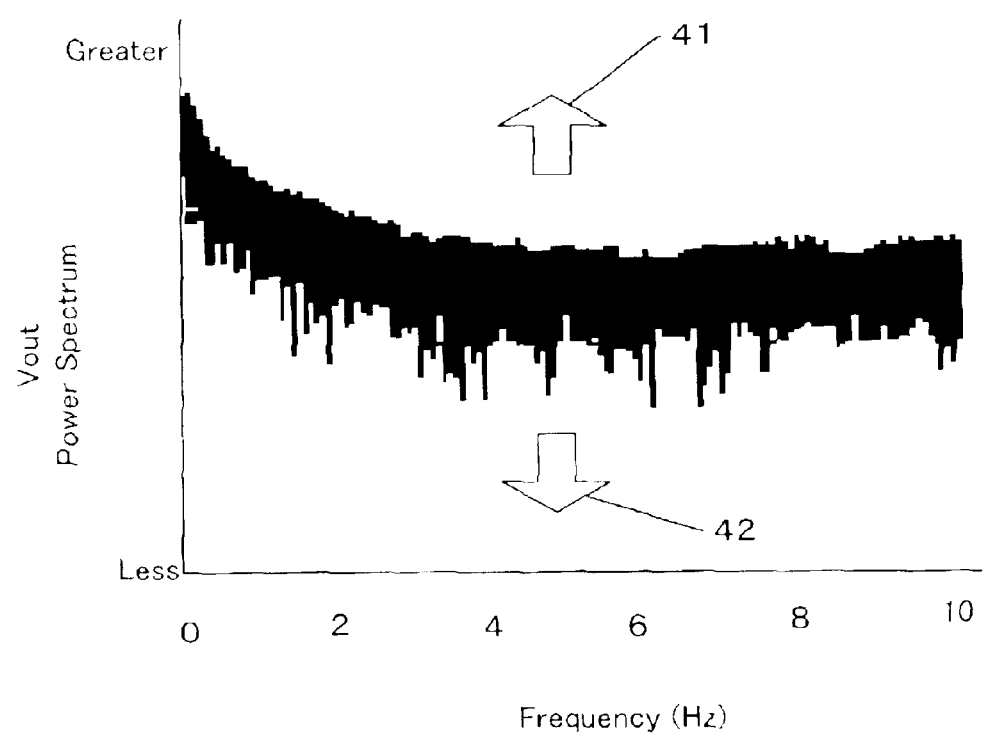
FIG. 3 shows one example of a frequency response of an output of the exhaust gas sensor.

FIG. 3 shows a result of Fourier transformation of the O2 sensor output Vout. If deterioration of the catalyst proceeds, the power spectrum of the sensor output Vout increases in the direction shown by an arrow 41. On the other hand, if the catalyst is a newer one, the power spectrum of the sensor output Vout decreases in the direction shown by an arrow 42. Based on this characteristic, deterioration of the catalyst can be determined.

If the O2 sensor deteriorates, a response delay of the O2 sensor increases. When the response delay increases, the power spectrum of the sensor output Vout decreases in the direction shown by the arrow 42.

Thus, when the O2 sensor deteriorates or is faulty, deterioration of the catalyst cannot be precisely detected since the power spectrum of the sensor output Vout decreases. In other words, a state in which the catalyst is new and a state in which the O2 sensor deteriorates cannot be distinguished by the power spectrum of the sensor output Vout.

Distinguishment of Deterioration of Catalyst from Failure of O2 Sensor

For the sake of easier understanding of the present invention, the scheme of distinguishing deterioration of the catalyst from a failure of the O2 sensor will be described. First, referring to FIGS. 4 and 5, the scheme of detecting deterioration of the catalyst will be described.

Figure 4:
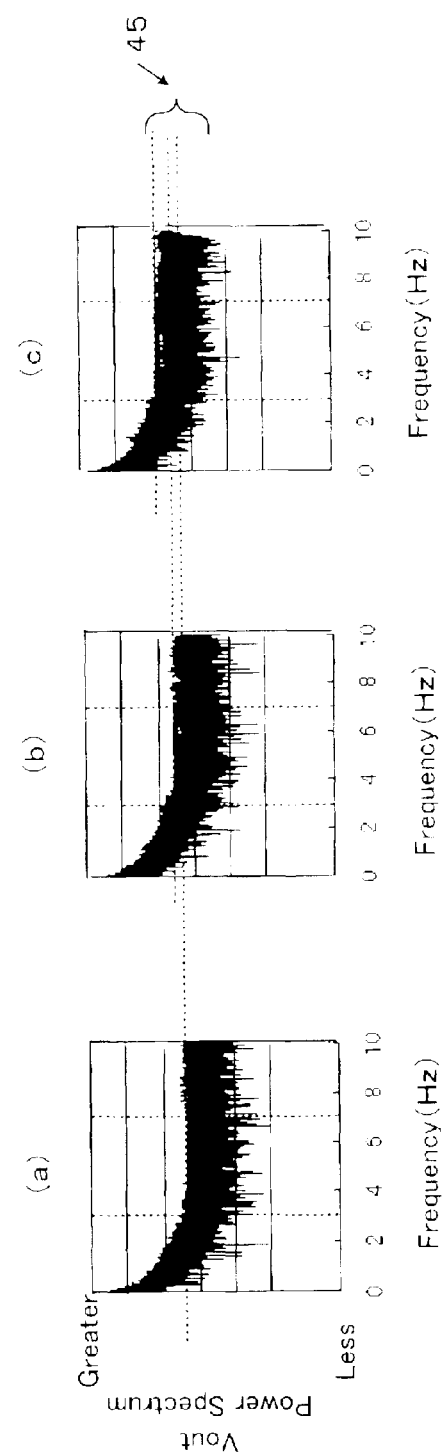
FIG. 4 shows that a frequency response of an output of an exhaust gas sensor varies according to the degree of deterioration of catalyst.

FIG. 4 shows a power spectrum of the O2 sensor output Vout (a) when the catalyst is new, (b) when the purification rate of the catalyst is sufficient, and (c) when the purification rate of the catalyst is insufficient. In FIGS. 4(*a*) to 4(*c*), the level of the power spectrum of the sensor output Vout in the frequency region of 3 through 7 Hz varies, which is indicated by the reference number 45.

Figure 5:
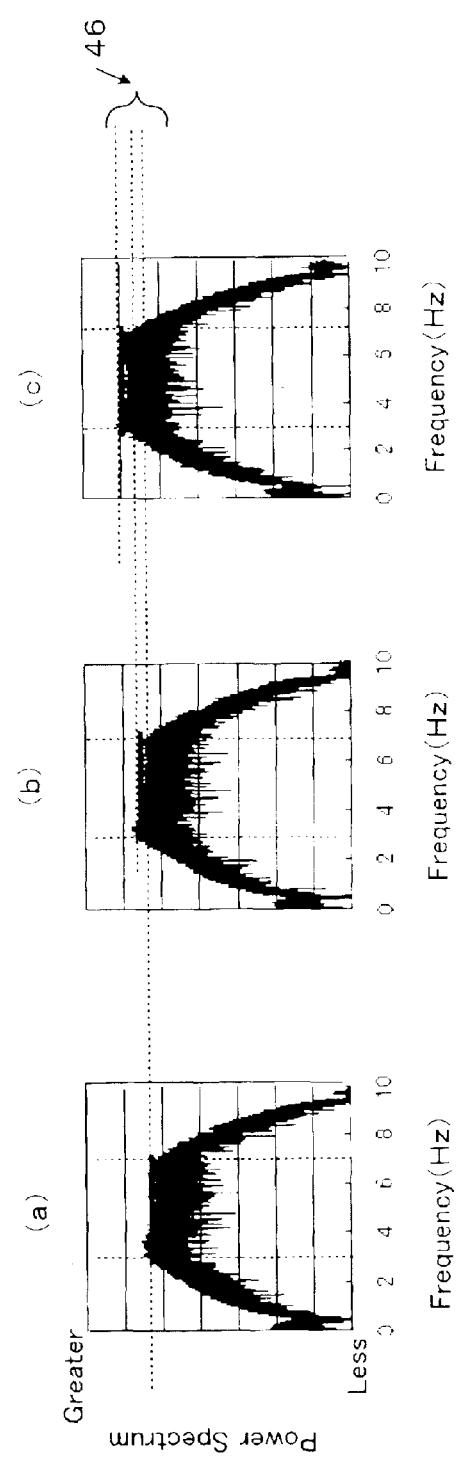
FIG. 5 shows that a frequency response of a filtered output of an exhaust gas sensor according to the degree of deterioration of catalyst.

FIGS. 5(*a*) to 5(*c*) show a result of filtering the sensor output Vout shown in FIGS. 4(*a*) to 4(*c*) with a band-pass filter, respectively. The power spectrum of the sensor output Vout in the frequency region of 3 through 7 Hz is emphasized by the filter. As shown by the reference number 46, as the catalyst deteriorates, the power spectrum of the sensor output Vout in the frequency regions 3 to 7 Hz increases. Thus, by evaluating the sensor output Vout in the frequency region of 3 to 7 Hz, it can be determined whether the catalyst is in a deteriorated state.

Figure 6:
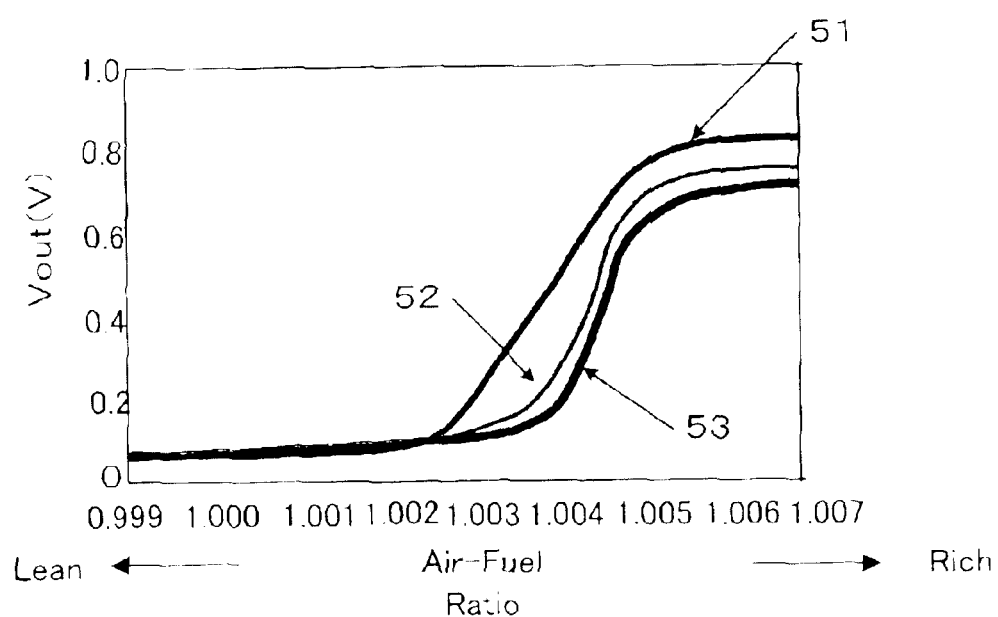
FIG. 6 shows one example of output characteristics of an exhaust gas sensor that vary according to element temperature.

The concept of determining a failure of the O2 sensor will be described. FIG. 6 shows output characteristics (referred to as Z curve) of the O2 sensor. A curve 51 shows a case in which the element temperature is 600°. A curve 52 shows a case in which the element temperature is 700°. A curve 53 shows a case in which the element temperature is 800°. It is seen that the amount of change in the output Vout of the O2 sensor is greater as the element temperature is lower.

Figure 7:
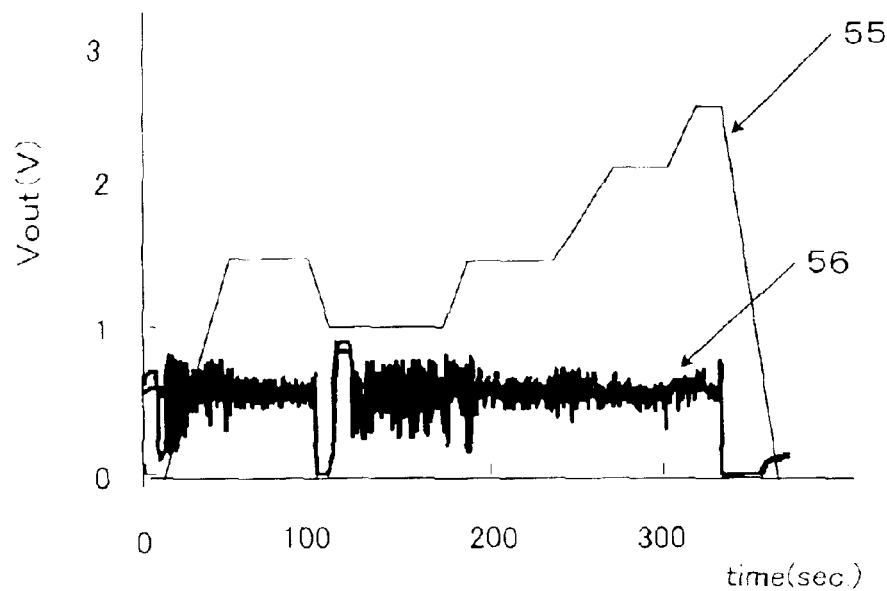
FIG. 7 shows behavior of an output of an exhaust gas sensor that varies according to an element temperature.
Figure 7:
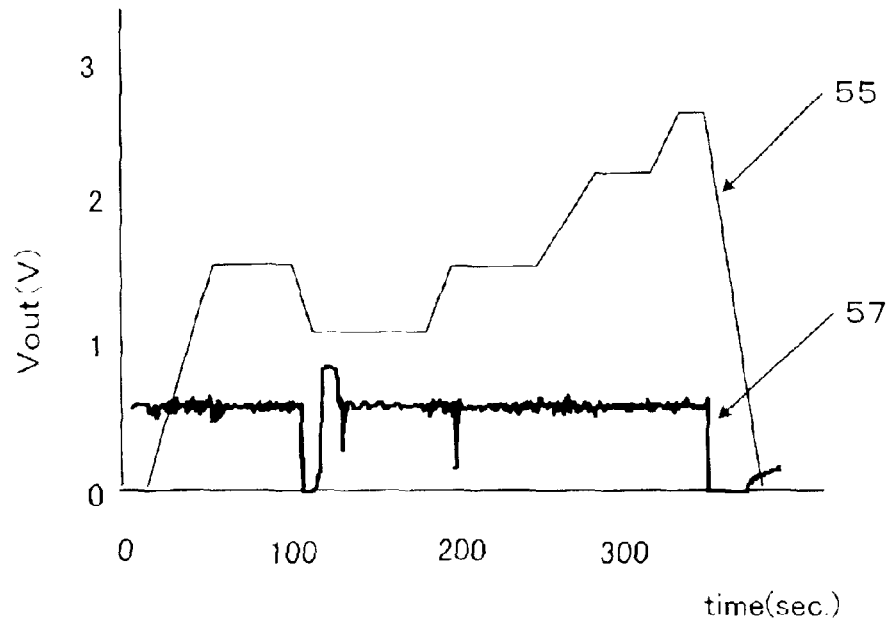

FIG. 7(*a*) shows behavior of the sensor output Vout when the element temperature is 600°. FIG. 7(*b*) shows behavior of the sensor output Vout when the element temperature is 800°. A graph 55 shows vehicle speed. Each of graphs 56 and 57 shows an output of the exhaust gas sensor. As seen from comparison between FIGS. 7(*a*) and 7(*b*), the amount of variation in the sensor output Vout when the element temperature is low is greater than the amount of variation in the sensor output Vout when the element temperature is high.

Figure 8:
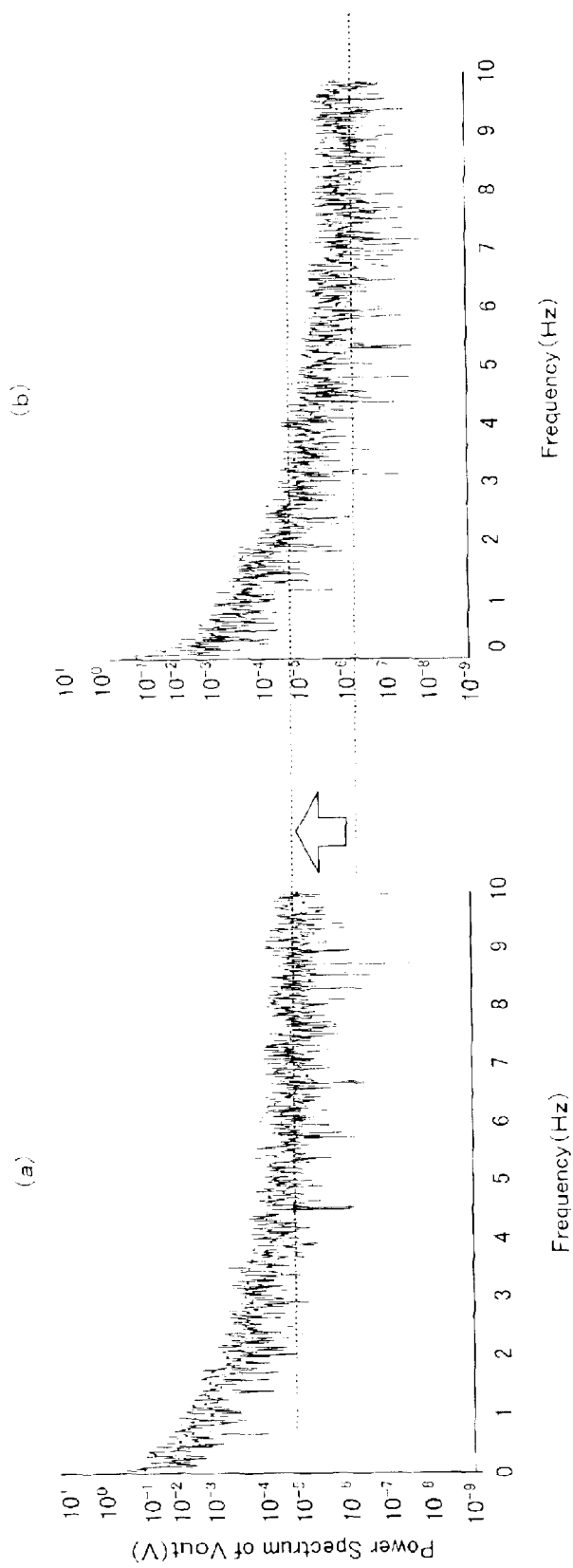
FIG. 8 shows a frequency response of an output of an exhaust gas sensor that varies according to an element temperature.

FIG. 8(*a*) shows a result of Fourier transformation of the sensor output Vout shown in FIG. 7(*a*). FIG. 8(*b*) shows a result of Fourier transformation of the sensor output Vout shown in FIG. 7(*b*). Because the amount of variation in the sensor output Vout is greater as the element temperature is lower, power of the sensor output Vout in each frequency also increases as the element temperature gets low.

Figure 9:
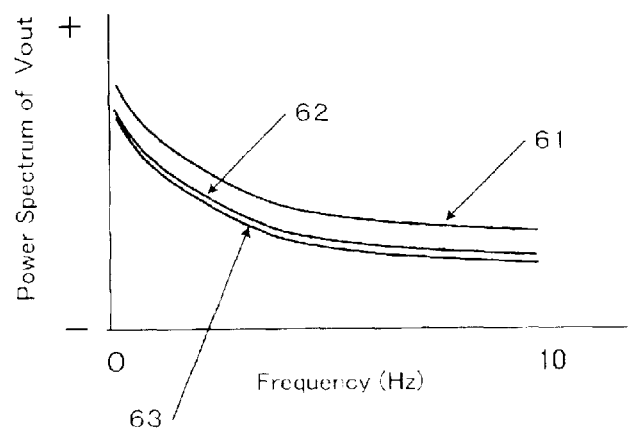
FIG. 9 shows an output of an exhaust gas sensor that varies according to both an element temperature and a fail/normal state of the exhaust gas sensor.

In FIG. 9, a curve 62 shows a power spectrum of the sensor output Vout when the element temperature is 600° and the O2 sensor is faulty (e.g., delay characteristics of the O2 sensor are great). A curve 61 shows a power spectrum of the sensor output Vout when the element temperature is 600° and the O2 sensor is normal. A curve 63 shows a power spectrum of the sensor output Vout when the element temperature is 800° and the O2 sensor is normal.

It is seen that the power spectrum of the sensor output Vout increases when the element temperature decreases. The increase in the power spectrum when the O2 sensor is faulty is smaller than the increase when the O2 sensor is normal. Therefore, by comparing the sensor output Vout when the element temperature is low (in this example, 600°) with the sensor output Vout when the element temperature is high (in this example, 800°), it can be determined whether the O2 sensor is faulty. If a ratio between the sensor output Vout when the element temperature is low and the sensor output Vout when the element temperature is high is less than a predetermined value, it indicates that the O2 sensor is faulty.

According to the scheme, a failure of the O2 sensor can be detected without changing the air-fuel ratio for the purpose of failure detection, which would otherwise reduce the purification rate of the catalyst. The amount of deleterious substances in exhaust gas does not increase because the air-fuel ratio is intentionally changed for the failure detection.

Figure 10:
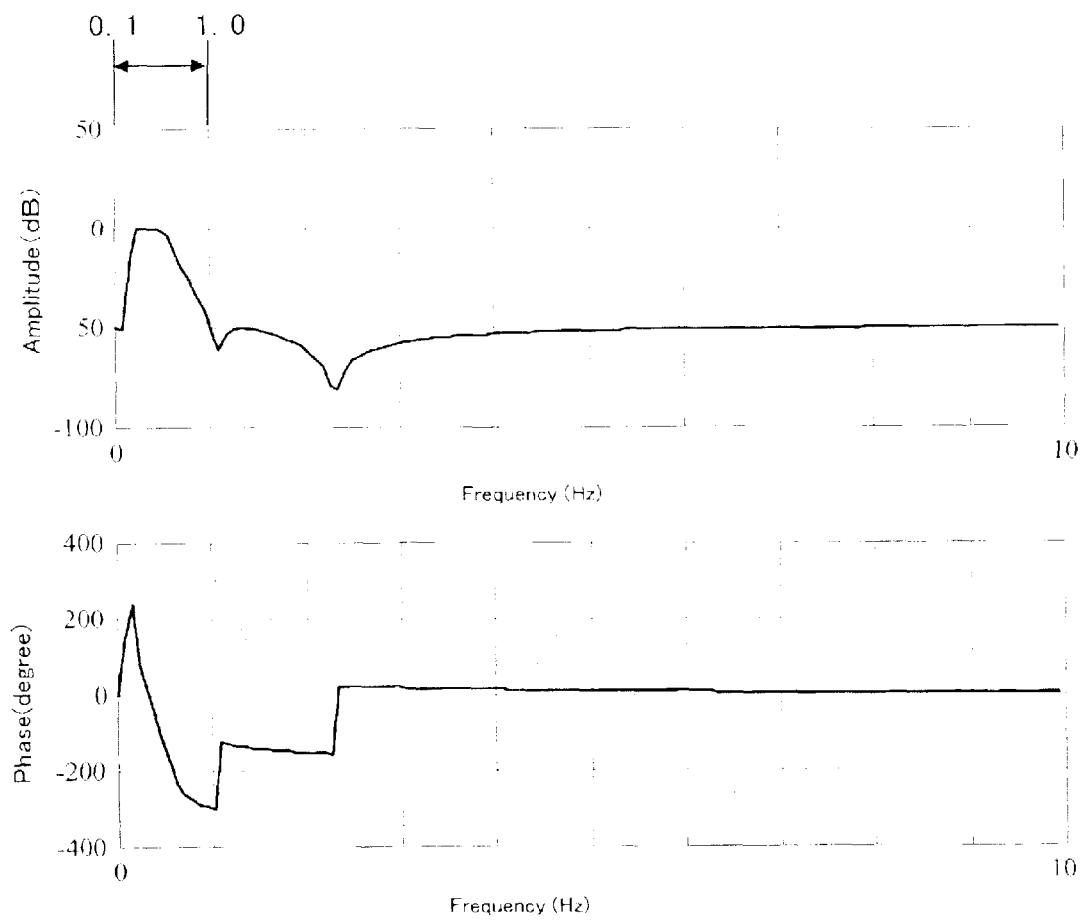
FIG. 10 shows filter characteristics of a band-pass filter according to one embodiment of the present invention.

In order to emphatically extract changes in the sensor output Vout when the element temperature is changed, a filtering process is applied to the sensor output Vout. FIG. 10 shows one example of filter characteristics of a band-pass filter used for the filtering process.

As shown in FIGS. 8 and 9, when the element temperature decreases, the power spectrum of the sensor output Vout increases in each frequency. However, as the frequency increases, the magnitude of the power spectrum in each frequency decreases due to low-pass characteristics of the catalyst and the O2 sensor. Since fluctuating components of the sensor output Vout at the time when the element temperature is changed need to be evaluated, it is preferable that steady components are removed. Therefore, a band-pass filter having characteristics as shown in FIG. 10 is used. In the example, the band-pass filter is designed to extract the power spectrum of the sensor output Vout in the frequency region of 0.1 to 1.0 Hz.

Figure 11:
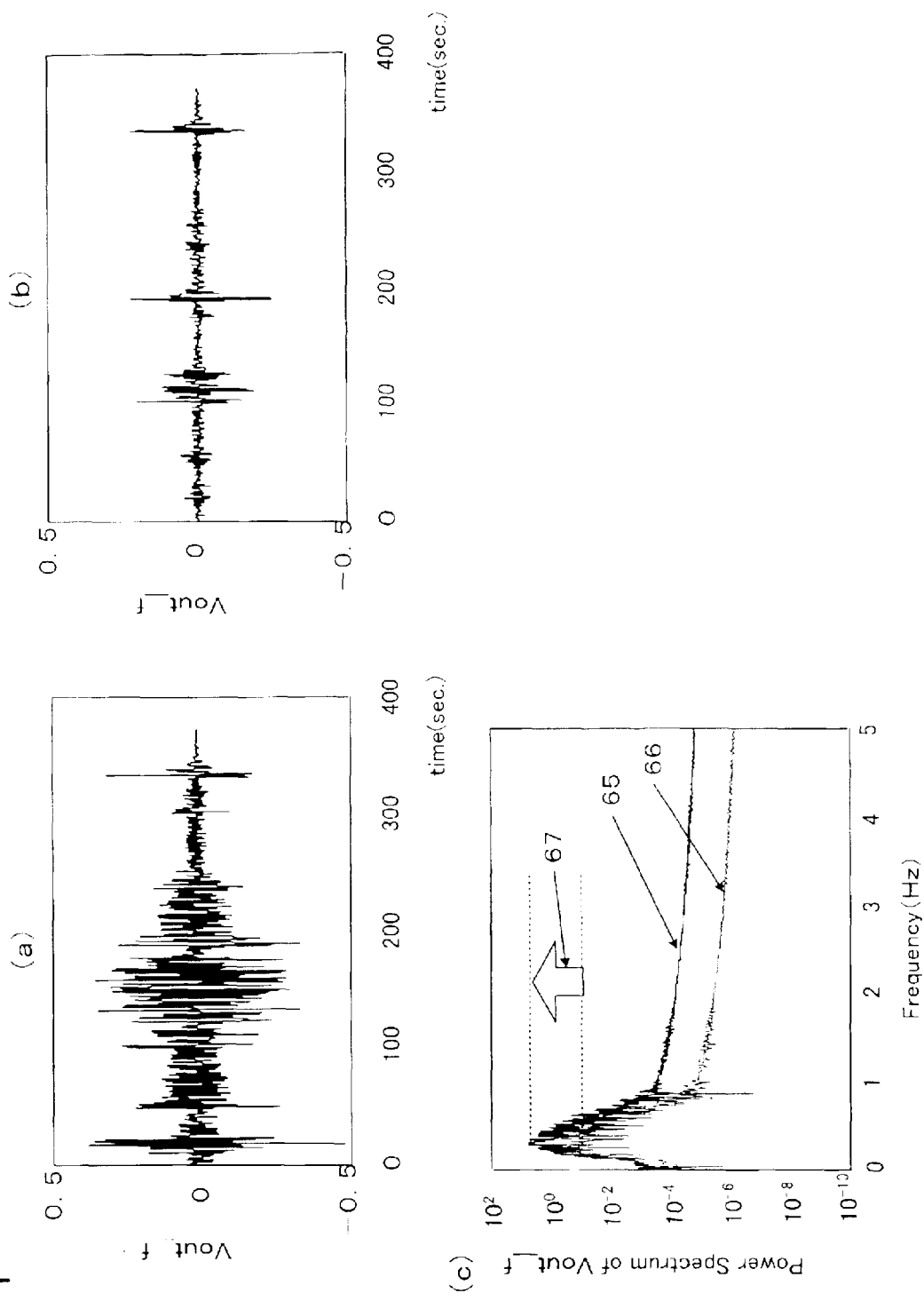
FIG. 11 shows an output of an exhaust gas sensor and a frequency response under different element temperatures.

FIG. 11(a) shows behavior of the filtered sensor output Vout_f when the element temperature is 600°. FIG. 11(b) shows behavior of the filtered sensor output Vout_f when the element temperature is 800°. FIG. 11(c) shows a result of Fourier transformation of the filtered sensor outputs Vout shown in FIGS. 11(a) and 11(b). A graph 65 shows a power spectrum of the sensor output Vout_f when the element temperature is 600°. A graph 66 shows a power spectrum of the sensor output Vout_f when the element temperature is 800°. By carrying out the filtering process, changes in the sensor output Vout that are caused by changes in the element temperature can be extracted as an amplitude difference 67.

Thus, deterioration of the catalyst affects the power spectrum of the O2 sensor output in the frequency region of 3 to 7 Hz. The deterioration of the catalyst can be determined by comparing detection values of the O2 sensor in the frequency region. On the other hand, a failure of the O2 sensor is detected by comparing detection values of the O2 sensor under different element temperatures. Therefore, it is possible to clearly distinguish deterioration of the catalyst from a failure of the O2 sensor.

Structure of Failure Detection Apparatus

Figure 12:
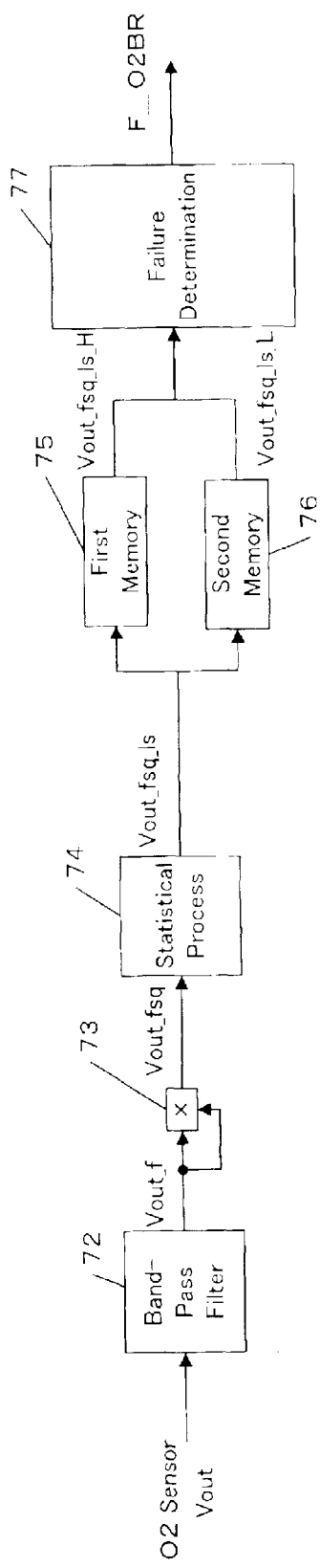
FIG. 12 is a functional block diagram of a failure detection apparatus in accordance with one embodiment of the present invention.

FIG. 12 is a functional block diagram showing an apparatus for detecting a failure of the O2 sensor according to one embodiment of the present invention. In a first pass, a state in which the element temperature is high is generated. A band-pass filter 72 is applied to the O2 sensor output. The band-pass filter 72 has characteristics as shown in FIG. 10. The band-pass filter 72 filters the sensor output Vout in accordance with equation (1) to generate Vout_f. Here, av1, av2, . . . , avn, bv0, bv1, . . . , bvm are filter coefficients predetermined by simulation or the like.

$$\text{Vout}\_f(k) = av1 \cdot \text{Vout}\_f(k-1) + av2 \cdot \text{Vout}\_f(k-2) + \ldots + avn \cdot \text{Vout}\_f(k-n) + bv0 \cdot \text{Vout}(k) + bv1 \cdot \text{Vout}(k-1) + \ldots + bvm \cdot \text{Vout}(k-m) \quad (1)$$

The filtered sensor output Vout_f(k) is squared by a multiplier 73 to generate Vout_fsq(k) as shown in equation (2).

$$\text{Vout}\_fsq(k) = \text{Vout}\_f(k) \times \text{Vout}\_f(k) \quad (2)$$

Alternatively, a low pass filter may be used instead of the band-pass filter. Since a band-pass filter capable of passing low frequency components tends to be unstable, a high pass filter and a low pass filter may be applied sequentially.

A statistical processing section 74 applies a successive least squares method to the squared sensor output Vout_fsq in accordance with equations (3) through (6) to determine a statistically processed sensor output Vout_fsq_1s.

$$\text{Vout}\_fsq\_1s(k) = \text{Vout}\_fsq\_1s(k-1) + KP(k) \cdot Eo2(k) \quad (3)$$

An error Eo2(k) shown in the equation (3) is expressed by equation (4). A gain coefficient KP(k) is calculated in accordance with equation (5).

$$Eo2(k) = \text{Vout}\_fsq\_1s(k-1) - \text{Vout}\_fsq(k) \quad (4)$$

$$KP(k) = \frac{P(k)}{1 + P(k)} \quad (5)$$

Here, "P" in the equation (5) is determined by equation (6).

$$P(k+1) = \frac{1}{\lambda_1}\left(1 - \frac{\lambda_2 \cdot P(k)}{\lambda_1 + \lambda_2 \cdot P(k)}\right) \cdot P(k) \quad (6)$$

Variations may occur in the O2 sensor output due to noise conditions. The sensor output may also vary according to the operating state of the vehicle/engine. The application of the successive least squares method can minimize the influence caused by such variations on the failure detection. Furthermore, by carrying out the successive least squares method, it is unnecessary to hold the filtered sensor output Vout_f after the statistical process in each cycle, thereby economizing on memory usage.

Alternatively, a non-successive least squares method may be used. The type of least squares method is determined by the values of $\lambda_1$ and $\lambda_2$ in the equation (6). For example, in a fixed gain method, $\lambda_1=1$ and $\lambda_2=0$. In a least-squares method, $\lambda_1=1$ and $\lambda_2=1$. In a decreasing gain method, $\lambda_1=1$ and $\lambda_2=\lambda$. In a weighted least squares method, $\lambda_1=\lambda$ and $\lambda_2=1$.

Vout_fsq_1s determined based on the sensor output Vout in a state in which the element temperature is high is held in a first memory 75 as Vout_fsq_1s_H. Thus, the first pass is completed.

In a second pass, a state in which the element temperature is low is generated. In a similar way to the first pass with the state in which the element temperature is high, the O2 sensor output Vout is subjected to the band-pass filter 72, the multiplier 73 and the statistical processing section 74. The statistically processed sensor output Vout_fsq_1s that is determined based on the sensor output Vout in the state in which the element temperature is low is held in a second memory 76 as Vout_fsq1s_L.

A failure determination section 77 reads out Vout_fsq_1s_H and Vout_fsq_1s_L stored in the first and second memories 75 and 76. The failure determination section 77 determines a ratio between Vout_fsq_1s_L and Vout_fsq_1s_H. If the ratio of Vout_fsq_1s_L/Vout_fsq_1s_H is less than a predetermined value RVFLS_BR, it indicates that a difference between the sensor output in the state in which the element temperature is high and the sensor output in the state in which the element temperature is low is small. This means that the sensor output hardly increases when the element temperature decreases. Therefore, it is determined that the O2 sensor is faulty. On the other hand, if the ratio of Vout_fsq_1s_L/Vout_fsq_1s_H is equal to or greater than the predetermined value RVFLS_BR, the failure determination section 77 determines that the O2 sensor is normal.

If it is determined that the O2 sensor is normal, a flag F_O2BR is set to zero. If it is determined that the O2 sensor is faulty, the flag F_O2BR is set to one. When the value of the flag F_O2BR is one, an MIL (warning light) may be lit to inform a passenger that the O2 sensor is faulty.

Structure of Element Temperature Controller

Figure 13:
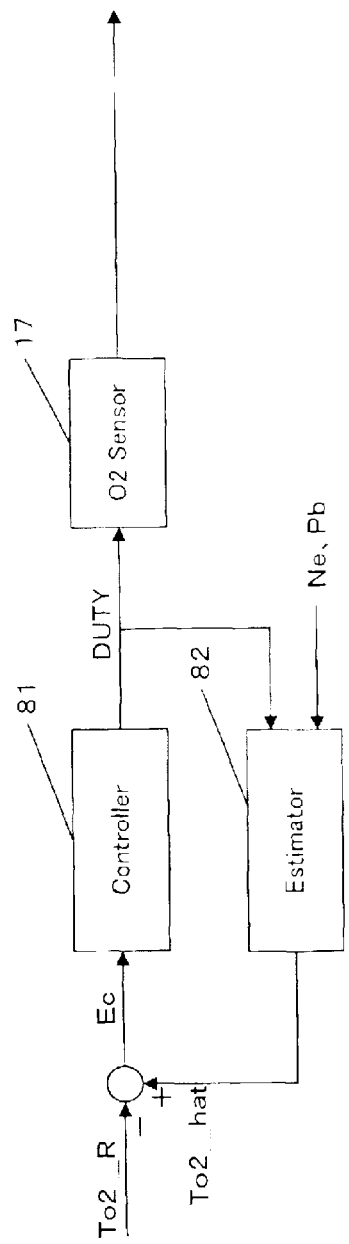
FIG. 13 is a control block diagram of an element temperature controller in accordance with one embodiment of the present invention.

FIG. 13 is a control block diagram of a controller for controlling the element temperature of the O2 sensor in accordance with one embodiment of the present invention. An object to be controlled or a plant of the element temperature control is the O2 sensor 17. Since it is difficult to directly measure the element temperature of the O2 sensor, the element temperature is estimated by an estimator 82. The estimator 82 calculates an estimated element temperature To2_hat based on the operating state of the internal combustion engine and an energization duty ratio DUTY that is determined in the previous cycle by a controller 81.

The estimated temperature To2_hat that is determined by the estimator 82 and a target element temperature To2_R are compared to determine an error Ec. The controller 81 determines the energization duty ratio DUTY for a heater based on the error Ec. The heater is provided in the O2 sensor 17. The heater is driven in accordance with the calculated energization duty ratio DUTY.

Thus, the controller 81 carries out feedback control for determining the duty ratio DUTY of energization of the heater so that the estimated temperature To2_hat converges to the target element temperature To2_R. In other words, feedback control for determining the duty ratio DUTY of energization of the heater is performed so that the error Ec between the estimated element temperature To2_hat and the target element temperature To2_R converges to zero.

The controller 81 carries out the feedback control using a response assignment control. By using the response assignment control, the accuracy and quick response of the control are maintained at high level. Especially, when the element temperature is reduced to a temperature lower than a normal temperature that is used for the normal operating state of the engine, the element temperature may overshoot toward a lower temperature and the O2 sensor may be inactivated. When the element temperature is increased to a temperature higher than the normal temperature, the heater may be damaged by overshoot of the heater temperature. According to the response assignment control, since the rate of convergence of the controlled variable to the target value can be designated, it is prevented that the O2 sensor is inactivated and that the heater is damaged.

The O2 sensor 17, which is an object to be controlled, can be modeled as shown in equation (7). The temperature To2 of the O2 sensor is defined as control output and the duty ratio DUTY of energization of the heater is defined as control input. The element of the O2 sensor is exposed to the exhaust gas, and is heated by the heater. Therefore, the element temperature To2 is determined based on the exhaust gas temperature Tex and the energization duty ratio that is calculated in the previous cycle.

The O2 sensor 17 is modeled as a discrete-time system model. Such modeling can make the algorithm of the element temperature control simple and suitable for computer processing.

$$To2(k+1) = Ao2\{To2(k) - Tex(k)\} + Bo2 \cdot DUTY(k) \quad (7)$$

Here, Ao2 and Bo2 are model parameters that are pre-identified with simulation or the like. Here, "k" is an identifier for identifying a control cycle. (k) indicates a current cycle and (k+1) indicates a next cycle.

Since it is difficult to directly measure the temperature To2 of the O2 sensor as described above, the estimated element temperature To2_hat calculated by the estimator 82 is used instead of the actual temperature To2. Since it is also difficult to directly measure the temperature Tex of the exhaust gas, an estimated exhaust gas temperature Tex_hat calculated by the estimator 82 is used instead of the actual exhaust gas temperature Tex.

An element temperature error Ec(k) is expressed as shown in the equation (8).

$$Ec(k) = To2\_hat(k) - To2\_R(k) \quad (8)$$

The controller 81 determines a switching function "σ" as shown in equation (9). The switching function specifies convergence behavior of the element temperature error Ec. Here, "pole" is a setting parameter of the switching function "σ", and is set to satisfy "−1<pole<1".

$$\sigma(k) = -pole \cdot Ec(k-1) + Ec(k) \quad (9)$$

The equation in the case of σ(k)=0 is called an equivalent input system, which specifies convergence characteristics of the element temperature error Ec or controlled variable. Assuming σ(k)=0, the equation (9) is transformed to the equation (10).

$$Ec(k-1) = \frac{1}{pole} \cdot Ec(k) \quad (10)$$

Figure 14:
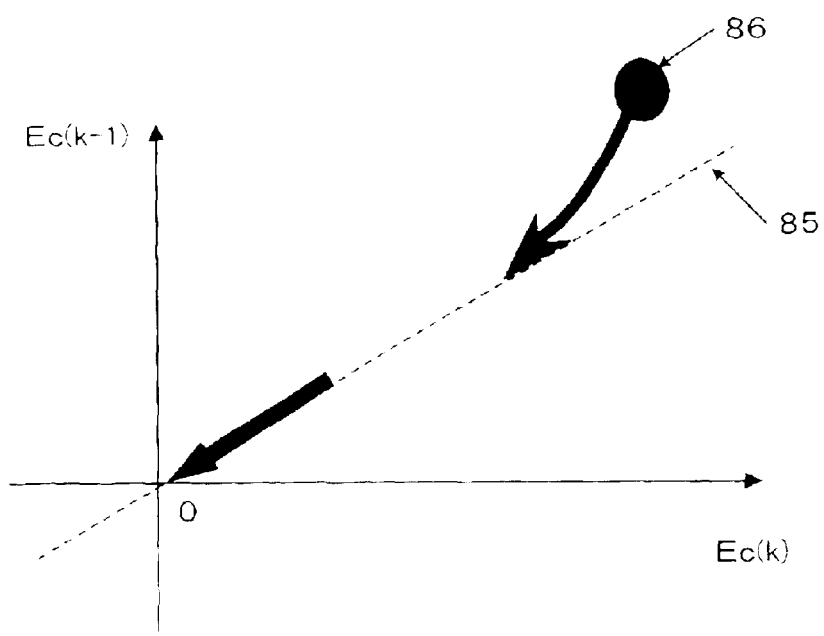
FIG. 14 schematically shows a switching line for response assignment control in accordance with one embodiment of the present invention.

Now, characteristics of the switching function σ will be described. In FIG. 14, the equation (10) is shown as a line 85 on a phase space with Ec(k-1) on the horizontal axis and Ec(k) on the vertical axis. This line 85 is referred to as a switching line. It is assumed that an initial value of a state quantity (Ec(k), Ec(k−1)) that is a combination of Ec(k) and Ec(k-1) is shown by a point 86. The response assignment control operates to place the state quantity shown by the point 86 on the switching line 85 and then restrain it on the switching line 85.

According to the response assignment control, since the state quantity is held on the switching line 85, the state quantity can highly stably converge to the origin 0 of the phase space without being affected by disturbances or the like. In other words, by restraining the state quantity (Ec(k), Ec(k−1)) on such a stable system having no input as shown in the equation (10), the estimated element temperature To2_hat can converge to the target element temperature TO2_R robustly against disturbances and modeling errors.

In the embodiment, since the phase space in which the switching function σ is represented is two-dimensional, the switching line is a straight line 85. If the phase space is three-dimensional, the switching line is expressed by a plane. If the phase space is four-dimensional or n-dimensional where n is greater than four, the switching line is expressed by a hyperplane.

The setting parameter "pole" can be variably selected. Reduction (convergence) characteristics of the element temperature error Ec can be specified by the setting parameter "pole".

Figure 15:
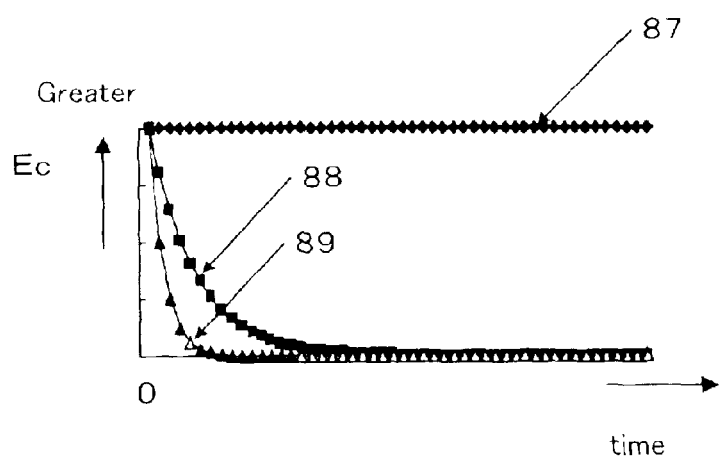
FIG. 15 shows response characteristics of a controlled quantity that depend on a setting parameter of a switching function in response assignment control in accordance with one embodiment of the present invention.

FIG. 15 shows one example of response assignment characteristics of the response assignment control. A line 87 shows a case in which the value of the pole is "1". A curve 88 shows a case in which the value of the pole is "0.8". A curve 89 shows a case in which the value of the pole is "0.5". As seen from the figure, the rate of convergence of the element temperature error Ec changes according to the value of the setting parameter "pole". It is seen that the convergence rate becomes faster as the absolute value of "pole" becomes smaller.

In order to cause the estimated element temperature To2_hat to converge to the target element temperature To2_R, the controller 81 determines the control input DUTY (e.g., heater energization duty ratio) in accordance with equation (11). As described above, DUTY is input into the modeled object shown by the equation (7). Here, Krch, Kadp and Ko2 indicate feedback coefficients. The coefficients can be determined in accordance with the optimal control theory or the like.

$$DUTY(k) = -Krch \cdot \sigma(k) - Kadp \cdot \sum_{i=0}^{k} \sigma(i) - Ko2 \cdot \text{To2\_hat}(k) \quad (11)$$

A first term (proportional term of the switching function σ) in the equation (11) indicates a reaching law input for placing the state quantity on the switching line. A second term (integration term of the switching function σ) indicates an adaptive law input for placing the state quantity on the switching line while suppressing modeling errors and disturbances. A third term indicates an equivalent control input for restraining the state quantity on the switching line.

The estimator 82 calculates the estimated element temperature To2_hat in accordance with the following equation (12). The equation (12) is based on the model equation shown in equation (7). Here, Ao2 and Bo2 are the same as those shown in equation (7), and indicate estimated parameters that are predetermined based on simulation or the like.

$$\text{To2\_hat}(k+1) = Ao2\{\text{To2\_hat}(k) - \text{Tex\_hat}(k)\} + Bo2 \cdot DUTY(k) \quad (12)$$

The estimated exhaust gas temperature Tex_hat(k) in the equation (12) is calculated in accordance with the following equation (13).

$$\text{Tex\_hat}(k) = Kex \cdot \text{Tex\_hat}(k-1) + (1-Kex) \cdot \text{Tex\_MAP}[Ne(k), PB(k)] \quad (13)$$

Figures 16, 17:
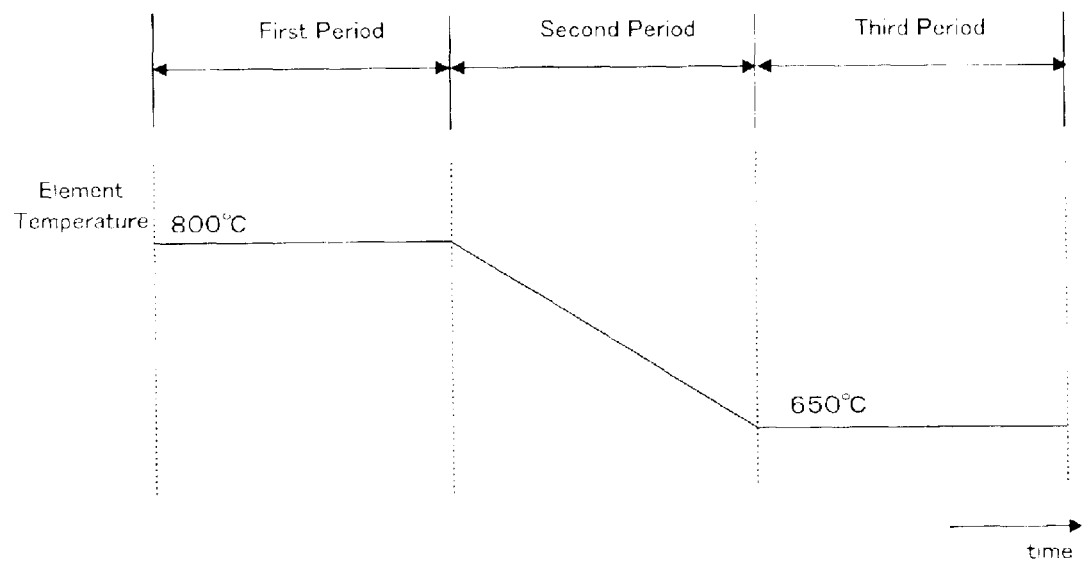
FIG. 16 shows one example of a steady exhaust gas temperature map used for estimating an element temperature in accordance with one embodiment of the present invention.
FIG. 17 schematically shows a flow for a failure detection process in accordance with one embodiment of the present invention.

Here, Tex_MAP[] indicates a value extracted from a steady exhaust gas temperature map Tex_MAP based on the engine rotational speed Ne and the intake manifold pressure Pb. FIG. 16 shows one example of the steady exhaust gas temperature map Tex_MAP. The steady exhaust gas temperature map Tex_MAP stores estimated temperatures of the exhaust gas when the engine is in a steady operating state. Here, Kex indicates an estimated parameter that is predetermined with simulation or the like.

The estimated element temperature To2_hat(k+1) calculated in the current cycle by the estimator 82 is used by the controller 81 so as to determine the energization duty ratio DUTY in the next cycle Operation Flow For the sake of easier understanding of flowcharts shown in FIGS. 18 through 21, a flow of the failure detection procedure in accordance with one embodiment of the invention is schematically shown in FIG. 17. In a first period, the element temperature is controlled to be maintained at a predetermined high temperature (e.g., 800°), which is a temperature used for the normal operating state of the engine. The O2 sensor output Vout is subjected to the filtering process and the statistical process.

In a second period after the first period has elapsed, control for reducing the element temperature to a predetermined low temperature (650° for example) is performed so as to detect a failure of the O2 sensor. In a third period after the second period has elapsed, the element temperature is controlled to be maintained at 650°. During a third period, the O2 sensor output Vout is subjected to the filtering process and the statistical process.

Figure 18:
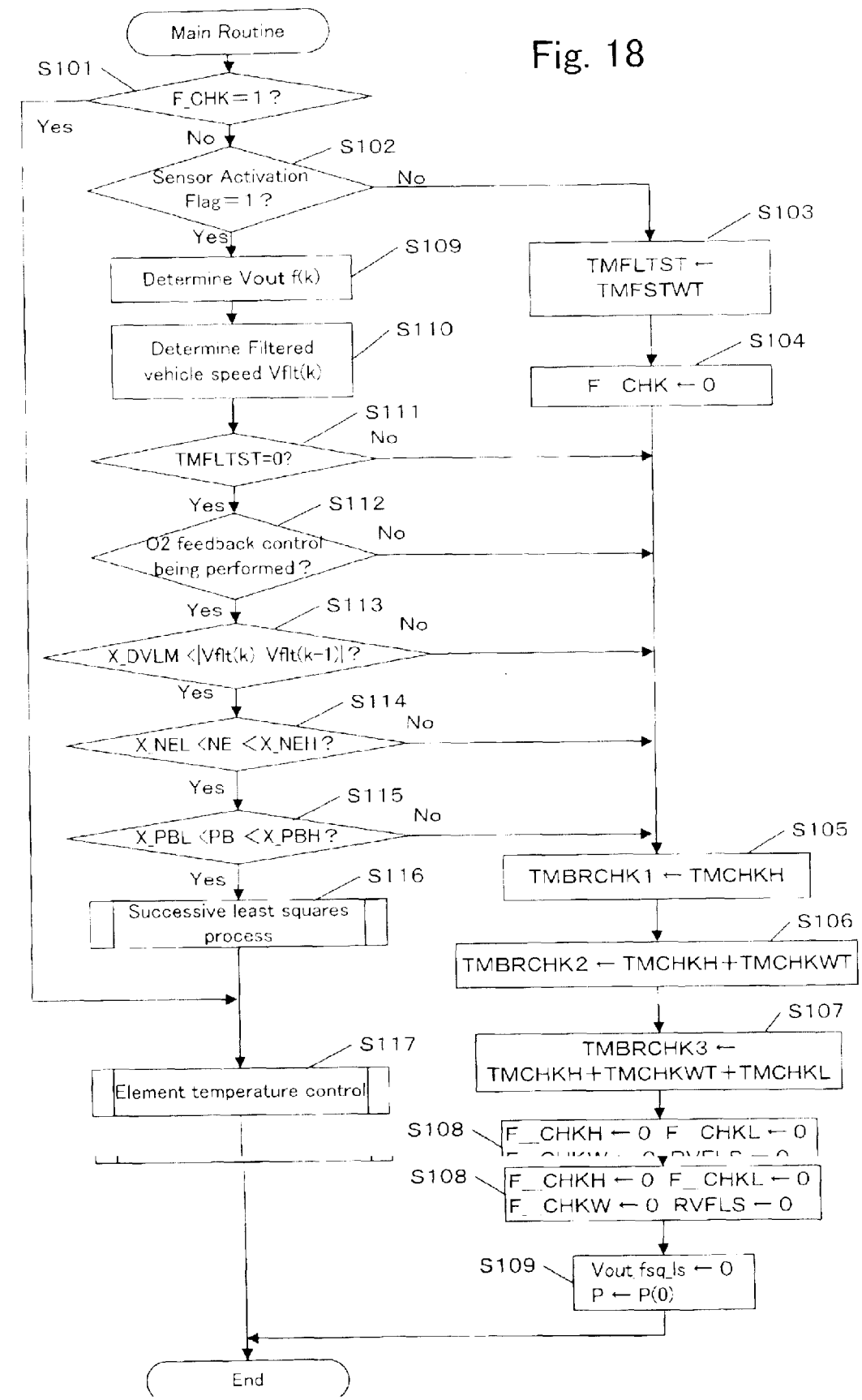
FIG. 18 is a flowchart showing a main routine of the failure detection process in accordance with one embodiment of the present invention.

FIG. 18 shows a main routine for detecting a failure of the O2 sensor in accordance with one embodiment of the present invention. In step S101, the value of a completion flag F_CHK is checked. The completion flag is a flag that is to be set to one when the failure determination process is completed. When the routine is carried out for the first time, the failure determination process has not yet been completed. Therefore, the answer of the determination step S101 is "No."

In step S102, it is determined whether the value of a sensor activation flag is one. The sensor activation flag is a flag that is to be set to one when the O2 sensor is activated. If the value of the sensor activation flag is zero, a predetermined value TMFSTWT is set in a timer TMFLTST (S103). Time (e.g., 1.0 second) required to stabilize the output of the band-pass filter is set in the predetermined value TMFSTWT. In step S104, the completion flag F_CHK is set to zero.

In steps S105 through 107, predetermined initial values are respectively set in timers TMBRCHK1, TMBRCHK2 and TMBRCHK3. The three timers measure the first, second and third periods, respectively. In step S108, flags and variables used for controlling the element temperature are initialized. In step S109, the statistically processed sensor output Vout_fsq_1s, which is to be calculated by the successive least squares method (FIG. 19), and a variable "P" are initialized.

If the value of the sensor activation flag is one in step S102 when the routine is re-entered, the O2 sensor output Vout is subjected to the filtering process in accordance with equation (1) to determine Vout_f(k) (S109). In step S110, in order to detect a state in which the vehicle is at cruise, a low pass filter is applied to vehicle speed Vp in accordance with the following equation (14) to determine a filtered vehicle speed Vflt. Here, af1, . . . , afn and bf0, . . . , bfm are low pass filter coefficients. A Butterworth filter or the like can be used as the low pass filter.

$$Vflt(k) = af1 \cdot Vflt(k-1) +, \ldots, + afn \cdot Vflt(k-n) + bf0 \cdot V(k) +, \ldots + bfm \cdot Vp(k-m) \quad (14)$$

In step S111, it is determined whether the timer TMFLTST activated in the step S103 indicates zero. If the timer does not indicate zero, the process proceeds to step S105, in which the first through third timers and the flags are initialized. If the timer indicates zero, it is determined whether O2 feedback control is being carried out (S112). If the O2 feedback control is being carried out, the process proceeds to step S113. Thus, when the output of the band-pass filter is stabilized and the air-fuel ratio is appropriately controlled by the O2 feedback control, the failure detection for the O2 sensor is carried out.

In step S113, the filtered vehicle speed Vflt(k) in the current cycle and the filtered vehicle speed Vflt(k−1) in the previous cycle are compared to determine whether a change in the vehicle speed is greater than a predetermined value X_DVLM. If the change in the vehicle speed is greater than the predetermined value X_DVLM, it indicates that the current operating state of the engine is not appropriate for carrying out the failure detection for the O2 sensor. Therefore, the process proceeds to step S105. In step S114, it is determined whether the engine rotational speed Ne is within a predetermined range (between a lower limit value X_NEL and an upper limit value X_NEH). If the engine rotational speed NE is not within the predetermined range, it indicates that the current operating state of the engine is not appropriate for carrying out the failure detection for the O2 sensor. Therefore, the process proceeds to step S105. In step S115, it is determined whether the intake manifold pressure PB is within a predetermined range (between a lower limit value X_PBL and an upper limit value X_PBH). If the intake manifold pressure PB is not within the predetermined range, it indicates that the current operating state of the engine is not appropriate for carrying out the failure detection for the O2 sensor. Therefore, the process proceeds to step S105.

Figure 19:
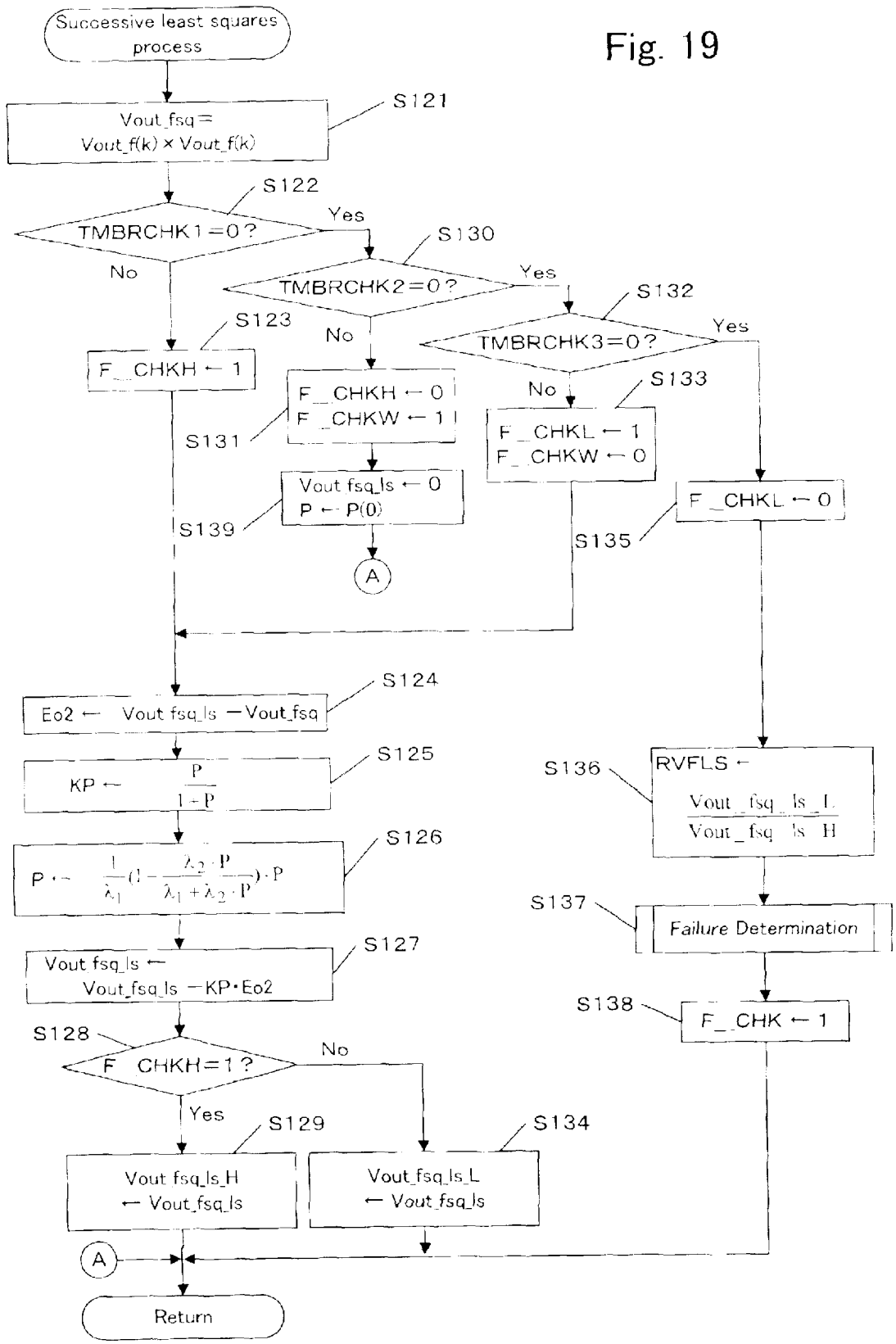
FIG. 19 is a flowchart showing a routine of a successive least squares method in accordance with one embodiment of the present invention.
Figure 21:
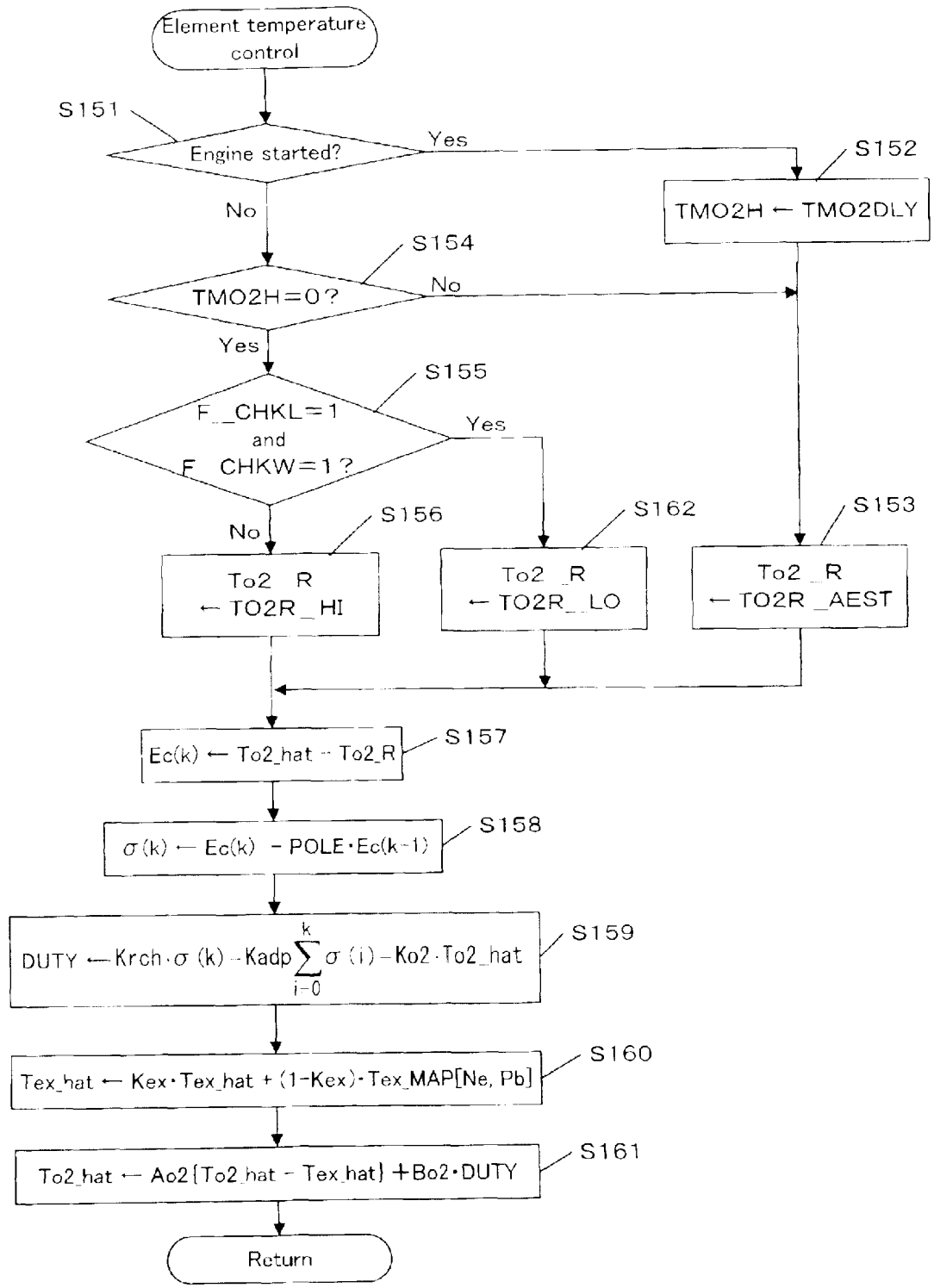
FIG. 21 is a flowchart showing an element temperature control routine in accordance with one embodiment of the present invention.

If all of the answers of the determination steps S113 through S115 are "Yes," the process proceeds to step S116, in which the successive least squares method is applied to the filtered sensor output Vout_f(k) (FIG. 19). The element temperature is then controlled in step S117 (FIG. 21).

If the completion flag F_CHK is one in step S101 when the routine is re-entered, the process proceeds to step S117 without making the failure determination. In step S117, the element temperature is controlled. Thus, the failure determination is carried out only once in a given driving cycle. The element temperature control is constantly carried out irrespective of the failure determination of the O2 sensor.

FIG. 19 shows a routine of the successive least squares process carried out in step S116. In step S121, the filtered sensor output Vout_f(k) is squared in accordance with equation (2) to determine Vout_fsq. In step S122, it is determined whether the timer TMBRCHK1 that measures the first period during which the element temperature is maintained at a high temperature indicates zero. If the timer does not indicate zero, a flag F_CHKH is set to one (S123). The flag F_CHKH has the value of one while the statistical process is carried out under the condition in which the element temperature is high.

In steps S124 through 127, the statistical process is carried out using the successive least squares method. In step S124, the error Eo2 is determined in accordance with equation (4). Vout_fsq_1s shown in step S124 indicates a statistically processed sensor output determined in the previous cycle. In step S125, the gain coefficient KP is determined in accordance with equation (5). Here, "P" shown in step S125 has been calculated in the previous cycle in accordance with equation (6). In step S126, "P" that is to be used in the next cycle is calculated.

In step S127, the statistically processed sensor output Vout_fsq_1s is calculated using the error Eo2 and the gain coefficient KP calculated in steps S124 and S125 in accordance with equation (3). When step S128 is carried out for the first time, the value of the flag F_CHKH is one. Therefore, the value of the calculated Vout_fsq_1s is stored in a memory as Vout_fsq_1s_H (S129).

If the first period has elapsed when the routine is re-entered, the answer of the determination step S122 is "Yes." The process proceeds to step S130, in which it is determined whether the timer TMBRCHK2 that measures the second period during which the element temperature is changed from a high temperature to a low temperature indicates zero. If the timer does not indicate zero, the flag F_CHKH is set to zero to indicate that the first period has elapsed. A flag F_CHKW is set to one to indicate that the second period is in progress (S131). The statistical process should not be carried out while the element temperature is being changed. In step S139, the statistically processed sensor output Vot_{13} fsq_1s and the variable P are initialized. The process then exits the routine.

If the second period has elapsed when the routine is re-entered, the answer of the determination step S130 is "Yes." The process proceeds to step S132, in which it is determined whether the timer TMBRCHK3 that measures the third period during which the element temperature is maintained at a low value indicates zero. If the timer does not indicate zero, the flag F_CHKW is set to zero to indicate that the second period has elapsed. A flag F_CHKL is set to one to indicate that the third period is in progress (S133).

In steps S124 through 127, as with the first period, the statistically processed sensor output Vout_fsq_1s is calculated by the successive least squares method. In the third period, since the value of the flag F_CHKH is maintained at zero, the answer of the determination step S128 is "No." The process proceeds to step S134, in which the value of Vout_fsq_1s calculated in step S127 is stored in a memory as Vout_fsq_1s_L.

If the third period has elapsed when the routine is re-entered, the answer of the determination step S132 is "Yes." The process proceeds to step S135, in which the flag F_CHKL is set to zero to indicate that the third period has elapsed.

Figure 20:
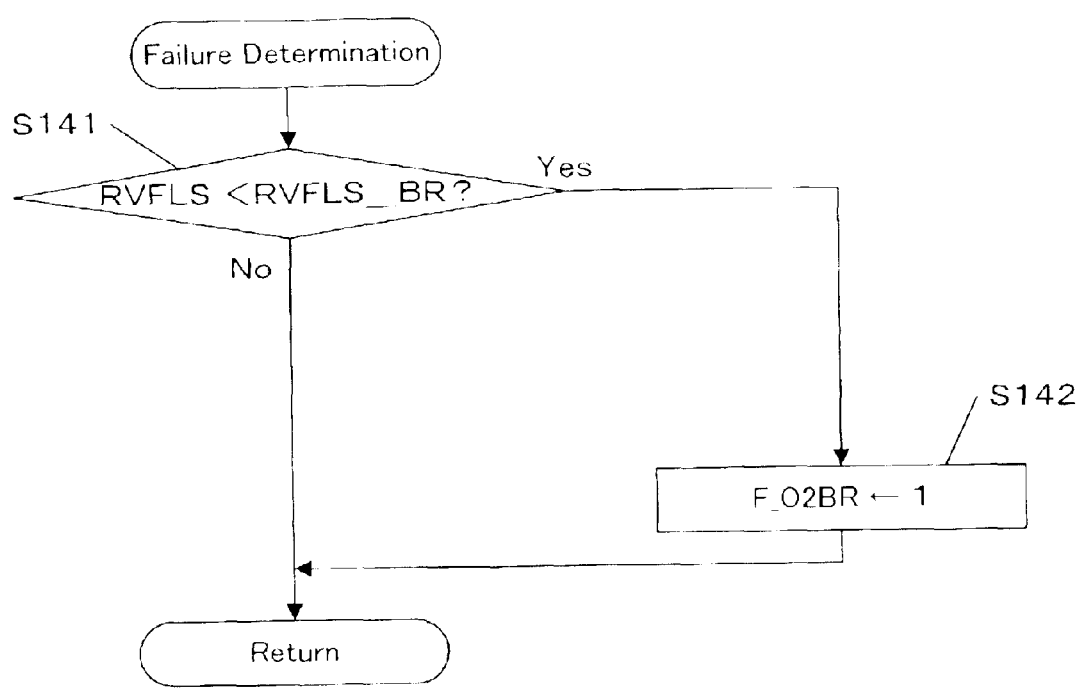
FIG. 20 is a flowchart showing a failure detection routine in accordance with one embodiment of the present invention.

In both states in which the element temperature is high and low, the statistically processed sensor outputs Vout_fsq_1s_L and Vout_fsq_1s_H are determined. In step S136, a ratio of the two sensor outputs is calculated by the equation of RVFLS=Vout_fsq_1s_L/Vout_fsq_1s_H. In step S137, the failure determination is carried out based on the calculated ratio RVFLS (FIG. 20). When the failure determination is completed, the completion flag F_CHK is set to one (S138).

FIG. 20 shows a failure determination routine carried out in step S137 shown in FIG. 19. In step S141, if the calculated ratio RVFLS is less than a predetermined value RVFLS_BR, it is determined that the O2 sensor is faulty. The failure flag F_O2BR is set to one (S142). In step S141, if the calculated ratio RVFLS is equal to or greater than the predetermined value RVFLS_BR, it is determined that the O2 sensor is normal, exiting the routine.

FIG. 21 shows an element temperature control routine carried out in step S117 shown in FIG. 18. In step S151, it is determined whether the engine is in the starting mode. If the engine is in the starting mode, a delay timer TMO2H is set to a predetermined value TMO2DLY (e.g., 10 seconds) (S152). When the engine is in the starting mode, water included in exhaust gas may hit the element of the O2 sensor. If the element temperature is abruptly increased when the element temperature is cooled by water, the O2 sensor may be damaged. Therefore, the element temperature is maintained at a predetermined value To2R_AEST (e.g., 600°) until the predetermined time TMO2DLY elapses (S153).

If the engine is not in the starting mode in step S151 and the period TMO2DLY set in the delay timer TMO2H has elapsed in step S154, the process proceeds to step S155. In step S155, if either the flag F_CHKL or the flag F_{13} CHKW is zero, it indicates that the first period is in progress. In the first period, the element temperature is maintained at a high value as described above. In step S156, the target element temperature To2_R is set to a predetermined high temperature TO2R_HI (e.g., 800°).

In step S155, if both the flags F_CHKL and F_CHKW are one, it indicates that the third period is in progress. In step S162, the target element temperature To2_R is set to a predetermined low temperature TO2R_LO (e.g., 650°).

In step S157, the element temperature error Ec is determined in accordance with equation (8). The estimated element temperature To2_hat shown in step S157 indicates an estimated element temperature To2_hat(k) calculated in the previous cycle. In step S158, the value of the switching function σ is determined in accordance with equation (9). In step S159, the energization duty ratio DUTY is calculated in accordance with equation (11). The estimated element temperature shown in step S159 also indicates the estimated element temperature To2_hat(k) calculated in the previous cycle.

In step S160, the estimated exhaust gas temperature Tex_hat(k) is calculated based on the estimated exhaust gas temperature Tex_hat(k−1) calculated in the previous cycle and the operating state of the engine (which is typically represented by intake manifold pressure Pb and engine rotational speed Ne) in the current cycle in accordance with equation (13). In step S161, the estimated element temperature To2_hat(k+1) is calculated based on the estimated element temperature To2_hat(k) calculated in the previous cycle, the estimated exhaust gas temperature Tex_hat(k) calculated in step S160, and the energization duty ratio DUTY(k) calculated in step S159 in accordance with equation (12). The calculated estimated element temperature To2_hat(k+1) is used for determining the energization duty ratio in the next cycle.

In the embodiment described above, the element temperature of the exhaust gas sensor is controlled from a high temperature to a low temperature. However, the present invention is not limited to the embodiment. The present invention can also be applied to the control for increasing the element temperature from a low temperature to a high temperature.

The invention may be applied to an engine to be used in a vessel-propelling machine such as an outboard motor in which a crankshaft is disposed in the perpendicular direction.

What is claimed is:

1. A controller for controlling a temperature of an element provided in an exhaust gas sensor, the exhaust gas sensor comprising a heater for heating the element, the controller comprising:
    an estimator for estimating an element temperature of the exhaust gas sensor; and
    a control unit configured to perform response assignment control based on the estimated element temperature to determine a duty ratio of energization of the heater.

2. The controller of claim 1, wherein the control unit is further configured to determine the energization duty ratio so that the element temperature converges to a target temperature.

3. The controller of claim 1, wherein the control unit is further configured to:
    determine a switching function for the response assignment control, the switching function specifying a response of the element temperature to a target temperature; and
    determine the energization duty ratio based on the integral of the switching function.

4. The controller of claim 1, wherein the control unit is further configured to determine the energization duty ratio so that the estimated element temperature converges to a target temperature.

5. The controller of claim 1,
    wherein the exhaust gas sensor is provided in an exhaust manifold of an engine,
    wherein the estimator is further configured to estimate the element temperature based on an operating state of the engine.

6. The controller of claim 1,
    wherein the exhaust gas sensor is provided in an exhaust manifold of an engine,
    wherein the estimator is further configured to estimate the element temperature based on a temperature of exhaust gas.

7. The controller of claim 6, wherein the estimator is further configured to:
    estimate the temperature of the exhaust gas based on an operating state of the engine; and
    estimate the element temperature based on the estimated exhaust gas temperature.

8. The controller of claim 7, further comprising a memory for storing a map in which predicted steady state temperatures of exhaust gas corresponding to steady operating states of the engine are provided,
    wherein the estimator is further configured to:
        acquire a current operating state of the engine;
        extract from the map a steady state temperature corresponding to the acquired operating state; and
        estimate the temperature of the exhaust gas based on the extracted steady state temperature.

9. The controller of claim 8, wherein the operating state of the engine is represented by rotational speed of the engine and pressure of an intake manifold of the engine.

10. A method for controlling a temperature of an element provided in an exhaust gas sensor, the exhaust gas sensor comprising a heater for heating the element, the method comprising the steps of:
    estimating an element temperature of the exhaust gas sensor; and
    performing response assignment control based on the estimated element temperature to determine a duty ratio of energization of the heater.

11. The method of claim 10, further comprising the step of:
    determining the energization duty ratio so that the element temperature converges to a target temperature.

12. The method of claim 10, further comprising the steps of:
    determining a switching function for the response assignment control, the switching function specifying a response of the element temperature to a target temperature; and
    determining the energization duty ratio based on the integral of the switching function.

13. The method of claim 10, further comprising the step of determining the energization duty ratio so that the estimated element temperature converges to a target temperature.

14. The method of claim 10,
    wherein the exhaust gas sensor is provided in an exhaust gas manifold of an engine,
    wherein the step of estimating the element temperature further comprises the step of estimating the element temperature based on an operating state of the engine.

15. The method of claim 10,
    wherein the exhaust gas sensor is provided in an exhaust gas manifold of an engine,
    wherein the step of estimating the element temperature further comprises the step of estimating the element temperature based on a temperature of exhaust gas.

16. The method of claim 15, wherein the step of estimating the element temperature based on a temperature of exhaust gas further comprises the steps of:

estimating the temperature of the exhaust gas based on an operating state of an engine; and estimating the element temperature based on the estimated exhaust gas temperature.

17. The method of claim 16, wherein the step of estimating the temperature of the exhaust gas further comprises the steps of:

storing in a memory a map in which predicted steady state temperatures of exhaust gas corresponding to steady operating states of the engine are provided;

acquiring a current operating state of the engine;

extracting from the map a steady state temperature corresponding to the acquired operating state; and estimating the temperature of the exhaust gas based on the extracted steady state temperature.

18. The method of claim 17, wherein the operating state of the engine is represented by rotational speed of the engine and pressure of an intake manifold of the engine.

19. A computer program stored on a computer readable medium for use in controlling a temperature of an element provided in an exhaust gas sensor, the exhaust gas sensor further comprising a heater for heating the element, the computer program comprising:

program code for estimating an element temperature of the exhaust gas sensor; and program code for performing response assignment control based on the estimated element temperature to determine a duty ratio of energization of the heater.

20. The computer program of claim 19, further comprising:

program code for determining the energization duty ratio so that the element temperature converges to a target temperature.

21. The computer program of claim 19, further comprising:

program code for determining a switching function for the response assignment control, the switching function specifying a response of the element temperature to a target temperature; and program code for determining the energization duty ratio based on the integral of the switching function.

22. The computer program of claim 19, further comprising:

program code for determining the energization duty ratio so that the estimated element temperature converges to a target temperature.

23. The computer program of claim 19, wherein the exhaust gas sensor is provided in an exhaust manifold of an engine, wherein the program code for estimating the element temperature further comprises program code for estimating the element temperature based on an operating state of the engine.

24. The computer program of claim 19, wherein the exhaust gas sensor is provided in an exhaust manifold of an engine, wherein the program code for estimating the element temperature further comprises program code for estimating the element temperature based on a temperature of exhaust gas.

25. The computer program of claim 24, wherein the program code for estimating the element temperature based on a temperature of exhaust gas further comprises:

program code for estimating the temperature of the exhaust gas based on an operating state of an engine; and program code for estimating the element temperature based on the estimated exhaust gas temperature.

26. The computer program of claim 25, further comprising a computer readable map for providing predicted steady state temperatures of exhaust gas corresponding to steady operating states of the engine, wherein the program code for estimating the exhaust gas temperature further comprises:

program code for acquiring a current operating state of the engine;

program code for extracting from the map a steady state temperature corresponding to the acquired operating state; and program code for estimating the temperature of the exhaust gas based on the extracted steady state temperature.

27. The computer program of claim 26, wherein the operating state of the engine is represented by rotational speed of the engine and pressure of an intake manifold of the engine.

* * * * *